United States Patent
Jay-Russell et al.

(10) Patent No.: US 11,234,681 B2
(45) Date of Patent: Feb. 1, 2022

(54) FISH TANK EFFLUENT SAMPLING SYSTEM

(71) Applicant: The Regents of the University of California, Oakland, CA (US)

(72) Inventors: Michele T. Jay-Russell, Davis, CA (US); Esteban Soto Martinez, Davis, CA (US); Elizabeth Antaki-Zukoski, Davis, CA (US); Christopher Zukoski, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 525 days.

(21) Appl. No.: 16/276,071

(22) Filed: Feb. 14, 2019

(65) Prior Publication Data

US 2019/0254640 A1    Aug. 22, 2019

Related U.S. Application Data

(60) Provisional application No. 62/631,622, filed on Feb. 16, 2018.

(51) Int. Cl.
| | |
|---|---|
| *A61B 10/00* | (2006.01) |
| *A01K 63/04* | (2006.01) |
| *A01G 31/02* | (2006.01) |
| *A01K 63/10* | (2017.01) |
| *C02F 3/32* | (2006.01) |

(Continued)

(52) U.S. Cl.
CPC .......... *A61B 10/0038* (2013.01); *A01G 31/02* (2013.01); *A01K 63/045* (2013.01); *A01K 63/10* (2017.01); *C02F 3/327* (2013.01); *A01G 2031/006* (2013.01); *A61B 2503/40* (2013.01); *C02F 2001/007* (2013.01); *C02F 2103/20* (2013.01); *C02F 2201/005* (2013.01); *C02F 2203/006* (2013.01); *C02F 2301/046* (2013.01)

(58) Field of Classification Search
CPC ............ A61B 10/0038; A61B 2503/40; A01K 63/045; A01K 63/10; A01G 31/02; A01G 2031/006; C02F 2103/20; C02F 3/327; C02F 2201/005; C02F 2001/007; C02F 2203/006; C02F 2209/001; C02F 2301/046; Y02P 60/21
USPC ......... 119/226–227; 210/92, 167.22, 167.23, 210/532.1, 533–535, 540; 422/533
See application file for complete search history.

(56) References Cited

U.S. PATENT DOCUMENTS

| | | | | |
|---|---|---|---|---|
| 1,063,754 | A * | 6/1913 | Weiss ..................... | B01D 21/02 |
| | | | | 210/534 |
| 5,290,437 | A * | 3/1994 | Lin ......................... | B01D 35/10 |
| | | | | 119/226 |

(Continued)

OTHER PUBLICATIONS

Fox et al. (2012) "A Preliminary Study of Microbial Water Quality Related to Food Safety in Recirculating Aquaponic Fish and Vegetable Production Systems" College of Tropical Agriculture and Human Resources, 11 pgs.

(Continued)

*Primary Examiner* — Matthew O Savage
(74) *Attorney, Agent, or Firm* — Brian E. Davy; Bozicevic, Field & Francis LLP

(57) ABSTRACT

Provided are fish tank effluent sampling systems, e.g., for use in recirculating aquaponics systems, methods of using same for sampling effluent, and kits for assembling such an effluent sampling system.

20 Claims, 9 Drawing Sheets

(51) Int. Cl.
*A01G 31/00* (2018.01)
*C02F 103/20* (2006.01)
*C02F 1/00* (2006.01)

(56) References Cited

U.S. PATENT DOCUMENTS

| | | | | |
|---|---|---|---|---|
| 5,636,595 A * | 6/1997 | Lunde | ............. | A01K 63/10 |
| | | | | 119/224 |
| 7,303,665 B1 * | 12/2007 | Claudio-Alvarado | ............. | |
| | | | | A01K 63/045 |
| | | | | 119/259 |
| 2017/0118964 A1 * | 5/2017 | Tsai | ............. | A01G 31/02 |

OTHER PUBLICATIONS

Pattillo (2017) "An Overview of Aquaponic Systems: Hydroponic Components" NCRAC Technical Bulletins, 11 pgs.

Tyson et al. (2012) "Aquaponics—Sustainable Vegetable and Fish Co-Production" Proc. Fla. State Hort. Soc., 125:381-385.

* cited by examiner

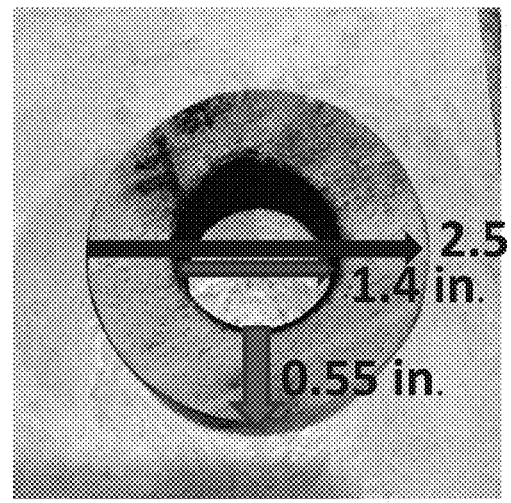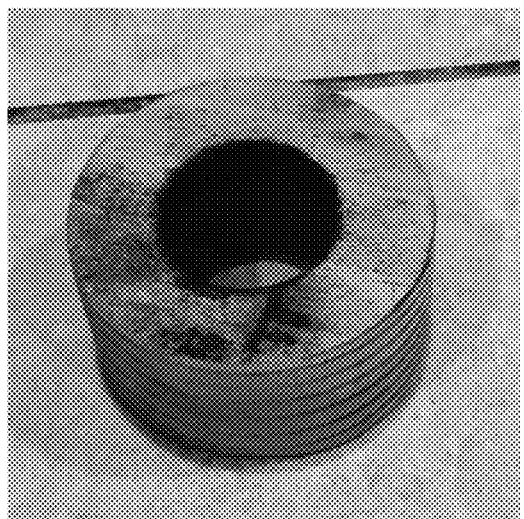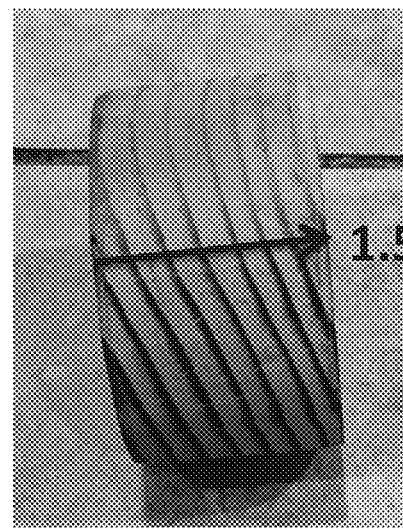
Fig. 8A-D

FISH TANK EFFLUENT SAMPLING SYSTEM

CROSS-REFERENCE TO RELATED APPLICATIONS

This application claims the benefit of U.S. Provisional Patent Application No. 62/631,622 filed Feb. 16, 2018, which application is incorporated herein by reference in its entirety.

STATEMENT OF GOVERNMENTAL SUPPORT

This invention was made with government support under Grant No. U19-FD004995, awarded by the Food and Drug Administration. The government has certain rights in the invention.

BACKGROUND

Aquaponics is derived from the combination of 'aquaculture' (fish) and 'hydroponics' (growing plants without soil), that result in a recirculating aquaponic system or RAS. In this type of system, fish effluent rich in nutrients fertilizes hydroponic beds, providing essential plant growth elements (Fox, et al., (2012) "A preliminary study of microbial water quality related to food safety in recirculating aquaponic fish and vegetable production systems." College of Tropical Agriculture and Human Resources, University of Hawaii at Manoa Food Safety and Technology. FST-51: 1-11. The advantages to using these types of systems include: 1) relatively smaller areas of land and soil are required to grow produce, 2) systems that can be utilized outdoors or in greenhouses with temperature regulation, 3) run-down building structures can be utilized as growing facilities, 4) fish and produce can be grown year-round, and 5) efficient use of water (Stivers, et al., (2016) *Food Prot. Trends.* 36: 242-247). Due to its recent popularity and growth, there is not enough information about aquaponics available, particularly in respect to nutrient management, specific plant-fish growth combinations, and most importantly, food safety. Existing data on foodborne bacterial pathogen populations in aquaponics are preliminary and consist of observational data (Fox, et al., 2012, supra).

SUMMARY

In one aspect, provided is a fish tank effluent sampling system. In some embodiments, the sampling system comprises:
(a) an outer pipe for effluent capture, and
(b) an inner pipe for fluid drainage;
wherein the outer pipe comprises:
(i) a bulkhead (3) capable of forming a drain orifice in the fish tank;
(ii) a connector pipe (5) that connects the bulkhead to a 3-way T connector (6);
(iii) a 3-way T connector (6);
(iv) a slip reducer (11) attached to the 3-way T connector (6), wherein the slip reducer seals around the inner pipe;
(v) a first valve (9) that connects to the 3-way T connector (6); and
(vi) a second valve (10) that connects to the first valve;
wherein the inner pipe comprises:
(i) a standpipe (2), wherein the standpipe is of a sufficient length to span the height of a desired water level in the tank and extend through the drain orifice in the tank into the outer pipe into an interior of the 3-way T connector (6), the standpipe connecting to
(ii); a 90° elbow connector (7) positioned within the 3-way T connector (6) in the outer pipe; and
(iii) a fluid drainage pipe (8) that connects to the 90° elbow connector (7), the fluid drainage pipe (8) extending from the interior of the 3-way T connector (6) at about 90° from the standpipe (2);
wherein the inner pipe and the outer pipe are sealed against fluid leakage. In some embodiments, the fluid in the inner pipe is not in fluid communication with the effluent in the outer pipe. In some embodiments, the fluid in the inner pipe is sealed against the effluent in the outer pipe. In some embodiments, the outer pipe further comprises a reducing fitting connecting the bulkhead (3) to the connector pipe (5). In some embodiments, the outer pipe further comprises a terminal adaptor (4) connecting the bulkhead (3) to the connector pipe (5). In some embodiments, the outer pipe further comprises a connector pipe (5) connecting the 3-way T connector (6) to the first valve (9). In some embodiments, the outer pipe further comprises a connector pipe (5) connecting the first valve (9) to the second valve (10). In some embodiments, the first valve (9) and the second valve (10) are a type of valve independently selected from the group consisting of a ball valve, a butterfly valve, a gate valve, a globe valve, a check valve and a stop valve. In some embodiments, the fluid drainage pipe (8) is further connected to a slip union (12). In some embodiments, the sampling system further comprises a screen insert in the drain orifice of the bulkhead (3) and sealing around the standpipe (2), wherein the screen insert comprises openings sufficiently large to allow fish feces and other effluent solids to flow into the outer pipe (e.g., to the second valve) and sufficiently small to prevent fish from entering the inner space of the outer pipe. In some embodiments, the inner pipe and the outer pipe do not comprise silicon. In some embodiments, the outer pipe has an inner diameter in the range of about 1.0 inches to about 4.0 inches, e.g., at least about 1.0 inch and up to about 1.5 in, 2.0 in, 2.5 in, 3.0 in, 3.5 in or 4.0 in. In some embodiments, the inner pipe has an inner diameter in the range of about 0.5 inches to about 2.0 inches, e.g., at least about 0.5 inch and up to about 1.0 in, 1.5 in or 2.0 in. In some embodiments, the ratio of the inner diameter of the outer pipe to the inner diameter of the inner pipe is from about 2:1 to about 4:1, e.g., 2:1, 2.5:1, 3:1, 3.5:1, 4:1. In some embodiments, the length of the outer pipe from the top of the bulkhead to the bottom of the second valve is in the range of about 10 inches to about 50 inches, e.g., at least about 10 inches and up to about 12, 14, 16, 18, 20, 22, 24, 26, 28, 30, 32, 34, 36, 38, 40, 42, 44, 46, 48 or 50 inches. In some embodiments, the length of the outer pipe from the top of the bulkhead to the center of the 3-way tee is in the range of about 5 inches to about 20 inches, e.g., at least about 5 inches and up to about 6, 7, 8, 9, 10, 11, 12, 13, 14, 15, 16, 17, 18, 19, 20 inches. In some embodiments, the length of the standpipe (2) is in the range of about 20 inches to about 50 inches, e.g., at least about 20 inches and up to about 25, 30, 35, 40, 45, 50 inches. In some embodiments, one or more of the elements (e.g., pipe fittings) of the outer pipe and/or the inner pipe are comprised of plastic pipe, e.g., poly vinyl chloride (PVC), chlorinated polyvinyl chlorine (CPVC), unplasticized PVC (UPVC), crosslinked polyethylene (PEX or XLPE) pipe, Polybutylene (PB), acrylonitrite-butadiene-styrene (ABS), high density polyethylene (HDPE) and POLYPIPE®. In some embodiments, one or more of the elements (e.g., pipe fittings) of the outer pipe and/or the inner pipe are comprised of metal pipe, e.g., copper, steel, iron or lead. In some embodiments, the sampling system further comprises a fish tank. In some embodiments, the fish tank has a volume in the range of about 5 L to about 500 L, e.g., at least about 5 L and up to about 10 L, 20 L, SOL, 75 L, 100 L, 110 L, 120 L, 130 L, 140 L, 150 L, 200 L, 250 L, 300 L, 350 L, 400 L, 450 L or 500 L. In some embodiments, the drain orifice of the fish tank is in a bottom surface of the tank. In some embodiments, the drain orifice of the fish tank is in a side surface of the tank. In some embodiments, the fish tank comprises one or more hydroponics rafts. In some embodiments, the sampling system further comprises a hydroponics tank, the hydroponics tank comprising one or more hydroponics rafts. In some embodiments, the hydroponics tank is in fluid communication with the fish tank. In some embodiments, the sampling system is in fluid communication with a recirculating aquaponics system (RAS), and effluent can be removed from the second valve while water continuously circulates from the fish tank to the hydroponics tank. In some embodiments, the water recirculates at a rate in the range of about 2 L/min to about 10 L/min. In some embodiments, the fish tank and the hydroponics tank are in fluid communication with a sump tank. Generally, in-flow of water from the sump tank is the same rate as the water draining down the standpipe. In some embodiments, the bottom surface of the fish tank is elevated sufficiently higher than the water surface level of the hydroponics tank to allow for water to flow from the fish tank to the hydroponics tank via gravity. In some embodiments, the bottom surface of the fish tank is elevated at least 12 inches higher, e.g., from about 12 inches to 13, 14, 15, 16, 17, 18, 19, 20, 21, 22, 24, or more, inches higher than the bottom or top surface of the hydroponics tank to allow for water to flow from the fish tank to the hydroponics tank via gravity.

In a further aspect, provided are methods of containing solid effluent from fish in a fish tank. In some embodiments, the methods comprise:

(a) providing an effluent sampling system of claim 20, wherein the fish tank comprises one or more live fish; and (b) allowing effluent including solids from the fish which have settled to the bottom of the fish tank to pass through the first valve (9) in the outer pipe and collect in the second valve (10); whereby the solid effluent from the fish in the fish tank is contained in the second valve (10). In some embodiments, surface water in the fish tank flows through the standpipe, e.g., and further to a hydroponics tank. In a related aspect, provided are methods of sampling effluent from a fish tank, the method comprising:

(a) providing an effluent sampling system of claim 20, wherein the fish tank comprises one or more live fish;

(b) allowing effluent including solids from the fish in the fish tank to pass through the first valve (9) in the outer pipe and collect in the second valve (10);

(c) blocking fluid flow through the first valve (9) and opening the second valve (10) to release the collected effluent; and (d) sampling the contents of the collected effluent. In some embodiments, the effluent comprises fish feces. In some embodiments, the feces is evaluated for the presence of a foodborne pathogen. In some embodiments, the foodborne pathogen is bacterial, viral and/or parasitic. In some embodiments, the foodborne pathogen is a bacterial pathogen from a bacteria genus selected from the group consisting of *Salmonella, Vibrio, Campylobacter, Escherichia coli, Listeria,* and *Yersinia*. In some embodiments, the collected effluent is evaluated for the quantities and/or ratios of one or more of carbon, oxygen, nitrogen, phosphorus, ammonia, nitrite, nitrates, pH, temperature, conductivity, dissolved oxygen, % oxygen, C:N ratio, nutrients, contaminants, toxins, heavy metals, pesticides and antibiotics. In some embodiments of the containment and sampling methods, the fish tank comprises one or more hydroponics rafts. In some embodiments of the containment and sampling methods, the fish tank is in fluid communication with a hydroponics tank. In some embodiments of the containment and sampling methods, the sampling system is in fluid communication with a recirculating aquaponics system (RAS), and effluent can be removed from the second valve while water continuously circulates from the fish tank to the hydroponics tank.

In a further aspect, provided is a kit. In some embodiments, the kit comprises:

(a) components (e.g., pipe fittings) for constructing an outer pipe, the outer pipe comprising:
  (i) a bulkhead (3) capable of forming a drain orifice in a fish tank;
  (ii) a connector pipe (5) that connects the bulkhead to a 3-way T connector (6);
  (iii) a 3-way T connector (6);
  (iv) a slip reducer (11) that is capable of sealing around the inner pipe;
  (v) a first valve (9) that connects to the 3-way T connector (6); and
  (vi) a second valve (10) that connects to the first valve; and (b) components (e.g., pipe fittings) for constructing an inner pipe, the inner pipe comprising:
  (i) a standpipe (2);
  (ii); a 90° elbow connector (7) that can be positioned within the 3-way T connector in the outer pipe; and
  (iii) a fluid intake pipe (8) that connects to the 90° elbow connector (7). In some embodiments, the kit further comprises (c) instructions for assembling a fish tank effluent sampling system, as described above and herein. In some embodiments, the 90° elbow connector (7) is provided fitted inside of the 3-way T connector (6). In some embodiments, the kit further comprises a cylindrical guide tool for fitting the 90° elbow connector (7) inside of the 3-way T connector (6). In some embodiments, the components for the outer pipe further comprise a reducing fitting capable of connecting the bulkhead (3) to the connector pipe (5). In some embodiments, the components for the outer pipe further comprise a connector pipe (5) capable of connecting the 3-way T connector (6) to the first valve (9). In some embodiments, the components for the outer pipe further comprises a connector pipe (5) connecting the first valve (9) to the second valve (10). In some embodiments, the first valve (9) and the second valve (10) are a type of valve independently selected from the group consisting of a ball valve, a butterfly valve, a gate valve, a globe valve, a check valve and a stop valve. In some embodiments, the kit further comprises a screen insert for fitting in the drain orifice of the bulkhead (3) and sealing around the standpipe (2), wherein the screen insert comprises openings sufficiently large to allow fish feces and other effluent solids to flow into the outer pipe and sufficiently small to prevent fish from entering the outer pipe. In some embodiments, the components for the inner pipe further comprise a slip union (12). In some embodiments, the components for the inner pipe and the outer pipe do not comprise silicon. In some embodiments, the outer pipe has an inner diameter in the range of about 1.0 inches to about 4.0 inches, e.g., at least about 1.0 inch and up to about 1.5 in, 2.0 in, 2.5 in, 3.0 in, 3.5 in or 4.0 in. In some embodiments, the inner pipe has an inner diameter in the range of about 0.5 inches to about 2.0 inches, e.g., at least about 0.5 inch and up to about 1.0 in, 1.5 in or 2.0 in. In some embodiments, the ratio of the inner diameter of the outer pipe to the inner diameter of the inner pipe is from about 2:1 to about 3:1. In some embodiments, the length of the outer pipe from the top of the bulkhead to the bottom of the second valve is in the range of about 10 inches to about 50 inches, e.g., at least about 10 inches and up to about 12, 14, 16, 18, 20, 22, 24, 26, 28, 30, 32, 34, 36, 38, 40, 42, 44, 46, 48 or 50 inches. In some embodiments, the length of the outer pipe from the top of the bulkhead to the center of the 3-way tee is in the range of about 5 inches to about 20 inches, e.g., at least about 5 inches and up to about 6, 7, 8, 9, 10, 11, 12, 13, 14, 15, 16, 17, 18, 19, 20 inches. In some embodiments, the length of the stand pipe is in the range of about 20 inches to about 50 inches, e.g., at least about 20 inches and up to about 25, 30, 35, 40, 45, 50 inches. In some embodiments, one or more of the elements (e.g., pipe fittings) of the outer pipe and/or the inner pipe are comprised of plastic pipe, e.g., poly vinyl chloride (PVC), chlorinated polyvinyl chlorine (CPVC), unplasticized PVC (UPVC), cross-linked polyethylene (PEX or XLPE) pipe, Polybutylene (PB), acrylonitrite-butadiene-styrene (ABS), high density polyethylene (HDPE) and POLYPIPE®. In some embodiments, one or more of the elements (e.g., pipe fittings) of the outer pipe and/or the inner pipe are comprised of metal pipe, e.g., copper, steel, iron or lead. In some embodiments, the kit further comprises PVC cement. In some embodiments, the kit further comprises a fish tank. In some embodiments, the fish tank has a volume in the range of about 5 L to about 500 L, e.g., at least about 5 L and up to about 10 L, 20 L, SOL, 75 L, 100 L, 110 L, 120 L, 130 L, 140 L, 150 L, 200 L, 250 L, 300 L, 350 L, 400 L, 450 L or 500 L. In some embodiments, the drain orifice of the fish tank is in a bottom surface of the tank. In some embodiments, the drain orifice of the fish tank is in a side surface of the tank. In some embodiments, the fish tank comprises one or more hydroponics rafts. In some embodiments, the kit further comprises a hydroponics tank, the hydroponics tank comprising one or more hydroponics rafts.

Definitions

As used herein, the terms "connected to" or "connects to" refers to direct (e.g., abutting) and indirect (e.g., not abutting) connections of plumbing components that are in fluid communication.

BRIEF DESCRIPTION OF THE DRAWINGS

FIGS. 8A-D provide several views and scale of an illustrative cylindrical insertion tool.

FIGS. 8A-D illustrate four views of the cylindrical guide or insertion tool, used to guide the insertion and positioning of the 90° elbow (7) into the 3-way T connector (6).

DETAILED DESCRIPTION

1. Introduction

Figure 1:
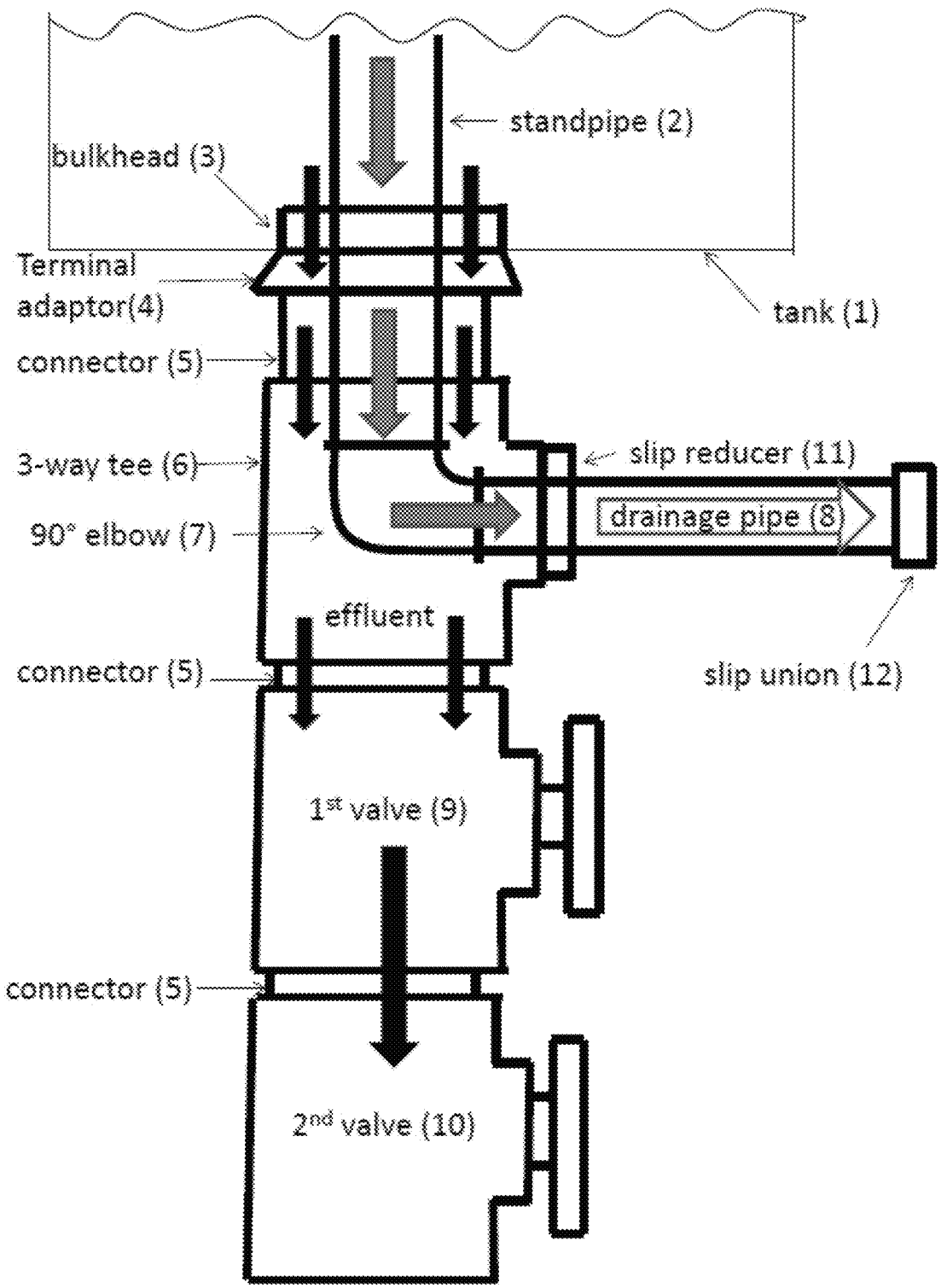
FIG. 1 illustrates a schematic of an illustrative fish tank effluent sampling system. The connecting pipes (5) are optional. Water from the surface of the fish tank, which is substantially free of solid effluent, flows down the standpipe (2) and out to the other side of the system, leading into the plant (hydroponics) tank and its filter. The 90° elbow (7) connected to the standpipe (2) is curved (e.g., sweeping), to minimize or eliminate solids collecting in the elbow, which can potentially lead bacterial growth. A terminal adaptor-male is threaded into the bulkhead and into a connector pipe (5). The connector pipe (5) is inserted into a 3-way T connector (6) that helps direct the drainage pipe 90° out to the side to the rest of the system from the fish tank. Inserted into the bottom of the 3-way T connector (6) is an optional connector pipe. In this embodiment, the diameters of the orifices of the 3-way T connector (6) are wider than the diameter of the first valve (9) and the second valve (10). The connecting pipes can have different diameters at each end, as needed. The first valve (9) and the second valve (10) can optionally be connected via a connector pipe (5).
Figure 2:
FIG. 2 illustrates an external view of the terminal adaptor (4), a connector pipe (5) that connects the bulkhead to a 3-way T connector (6); and the 3-way T connector (6).
Figure 3:
FIG. 3 illustrates of the 3-way T connector (6), connected to the first valve (9) and the second valve (10), as well as the drainage pipe (8) connected to a slip union (12). Arrows show the flow of water. Blue arrow=slip union (12) (threaded in the middle) for easy disconnect from the fish to the plants for cleaning, green arrow=water moving from the fish tank standpipe through the 90 degree elbow (7) and out the T-valve (6) to the plant tank, Red arrow=water moving from a plant tank to a sump tank and then getting pumped back into the fish tank.
Figure 4:
FIG. 4 illustrates the effluent sampling system stabilized by a brace (e.g., a metal unitrut). Fastening the valves against a brace, e.g., that is attached to a scaffolding or support under the fish tank, provides stability for the valves when opening and closing them, preventing twisting and breaking the seals.
Figure 5:
FIG. 5 illustrates view of total system, including fish tanks, hydroponic tanks and sump tanks. Blue arrow=Fish tank bank containing 6 individual tanks, Green arrows=Plant tank bank containing 6 individual tanks, Purple arrow=sump tanks that contain, e.g., pump, tank heater, and bioballs for each system.
Figure 6:
FIG. 6 illustrates a side view of the standpipe (2). The slit on the side of the stand pipe facilitates regulation of the water level. The slip cap on top of the standpipe with drilled holes provides a safety mechanism to prevent the system from over flowing, e.g., in case there is a clog or a pump fails. A screen insert with holes surrounds the stand pipe and is within the inner orifice of the bulkhead. The holes in the screen insert are large enough to allow for the passage of solid effluent (e.g., fish feces) into the outer pipe.
Figure 7:
FIG. 7 illustrates a top view of the standpipe (2). A screen insert with holes surrounds the stand pipe and is within the inner orifice of the bulkhead.

In order to study pathogens in fish effluent and to establish good agricultural practices (GAPs), existing aquaculture tanks were standardized at the Center for Aquatic Biology and Aquaculture (CABA) facility so that each system was a replicate of one another. Two banks, each with six 35-gallon tanks were separated to prevent external contamination. The bank that was used for the fish was then raised up on each leg with two 8 in.×8 in.×8 in. cinder blocks (e.g., to raise each fish tank 16 inches) and one 2 in.×6 in.×12 ft. pressure-treated board. The plant side also was raised on two 2 in. cinder blocks, e.g., to raise each hydroponics tank 4 in., e.g., to accommodate the sump tank. In addition to this, the tanks used for the fish had different diameter drains, so they were drilled out and replaced with 2 in. bulk heads. Due to the tanks being raised and separated, we developed a fish tank effluent sampling system to properly sample without cross contamination the fecal material that collects on the bottom of the fish tank. In the fecal release valve construction described herein, the RAS can still circulate water, but fecal material could be collected from the bottom of the fish tank by using a valve system instead of a gravel suction. From this point, pipe was then constructed to flow water from the fish to the plant tanks by gravity, to then be pumped back to the fish tanks, resulting in a closed-loop system.

Accordingly, provided are fish tank effluent sampling systems, e.g., of use for recirculating aquaponic systems (RAS). The valve system described herein was designed to collect fecal material produced by foodborne pathogens (e.g., *Salmonella*) that may be in fish feces. Fish feces provide nitrogenous nutrients for leafy green plant production in a closed RAS. This valve system was built to identify and prevent cross-contamination of each RAS during the experimental collection periods.

Advantages of the fish tank effluent sampling systems described herein include the containment and tracking of foodborne pathogens within these types of RAS production systems and the ability to sample, e.g., at periodic time intervals, fish fecal material, without disrupting water flow. Further, the fish tank effluent sampling systems decrease the potential cross-contamination by introducing gravel suction systems to collect samples.

In one illustrative and non-limiting embodiment, under a 35 gallon fiberglass tank, containing fish, provided is a 2 inch bulkhead that serves as a tank drain. Screwed into the bulkhead, there is a 2 inch×2.5 inch PVC connector. There is then a 2.5 inch PVC pipe connected into the bottom of the connector, leading to a 2.5 inch PVC 3-way T. Connected to the bottom of the T, there is a PVC reducer (2.5 inch to 2 inch) that connects to a small section of 2 inch PVC. Connected in serial to the reducer, are two 2 inch PVC valves attached with small intervening sections of 2 inch PVC pipe. Stemming from just below the water level of the fish tank, a 1 inch PVC vertical (relative to the water surface) standpipe is plumbed down to the middle of the 2.5 inch PVC 3-way T, connecting to a curved (e.g., sweeping) 1 inch 90° PVC elbow. The elbow is connected to a 1 inch PVC pipe exiting from the 3-way T at 90° from the stand pipe (e.g., horizontal relative to the water surface) through a modified 1 inch PVC slip reducer. This 1 inch pipe then connects to a 1 inch slip union, which connects with the rest of the 1 inch plumbing for the RAS flowing to the plant tank. A schematic of the effluent sampling system is provided, e.g., in FIG. 1.

2. Sampling System

The fish tank effluent sampling systems comprise an inner pipe for fluid drainage and an outer pipe for effluent capture. The inner pipe is fitted within certain sections of the outer pipe and there is sufficient difference in diameter between the outer diameter of the inner pipe and the inner diameter of the outer pipe such that effluent solids (e.g., fish feces) can freely flow around the inner pipe, reaching the interior of the second valve (10) at the bottom of the outer pipe. Generally, the fluid in the inner pipe is not in fluid communication with the effluent in the outer pipe. Generally, the fluid in the inner pipe is sealed against the effluent in the outer pipe. Both the inner pipe and the outer pipe are fitted within a drainage orifice of a fish tank. In some embodiments, the ratio of the inner diameter of the outer pipe to the inner diameter of the inner pipe is from about 2:1 to about 4:1, e.g., 2:1, 2.5:1, 3:1, 3.5:1, 4:1.

The inner pipe and outer pipe can be made of the same or different materials. Additionally, the elements connecting the inner pipe or the outer pipe can be made of the same or different materials. In some embodiments, one or more of the elements (e.g., pipe fittings) of the outer pipe (including the bulkhead) and/or the inner pipe are comprised of plastic pipe, e.g., poly vinyl chloride (PVC), chlorinated polyvinyl chlorine (CPVC), unplasticized PVC (UPVC), crosslinked polyethylene (PEX or XLPE) pipe, Polybutylene (PB), acrylonitrite-butadiene-styrene (ABS), high density polyethylene (HDPE) and POLYPIPE®. In some embodiments, one or more of the elements (e.g., pipe fittings) of the outer pipe and/or the inner pipe are comprised of metal pipe, e.g., copper, steel, iron or lead. When using pipe elements made of polymers, the pipe elements can be sealed or glued using PVC cement. Silicon sealants are generally avoided because the silicon has a tendency to stick to solid effluent.

The fish tank effluent sampling system can be used for fish tanks that are part of individual or personal scale aquaponics systems, or for fish tanks that are part of industrial scale aquaponics systems. In some embodiments, the fish tank has a volume in the range of about 5 L to about 500 L, e.g., at least about 5 L and up to about 10 L, 20 L, SOL, 75 L, 100 L, 110 L, 120 L, 130 L, 140 L, 150 L, 200 L, 250 L, 300 L, 350 L, 400 L, 450 L or 500 L. In various embodiments, the effluent sampling system can be mounted to a drain orifice in the bottom surface or in a side surface of a fish tank.

In various embodiments, the effluent sampling system is mounted on a scaffolding or a brace. The scaffolding or brace can provide additional stability and strength for the sampling system, especially when switching the valves between on and off positions for sampling and then sealing.

a. Inner Pipe

The inner pipe comprises (i) a standpipe (2) connected to a (ii) a 90° elbow (7) connected to a (iii) fluid drainage pipe (8). The standpipe is positioned in a fish tank vertically (perpendicularly) relative to the surface of the water, with the top of the standpipe at the level of or just below the surface of the water (e.g., within about 5, 4, 3, 2 or 1 inches below the surface of the water). In some embodiments, the stand pipe is at the same level as the water surface. The top of the standpipe is at a level that allows for drainage of water through the standpipe to the plant tanks.

Water at or near the surface of the water, and which is substantially free of solids (e.g., fish feces) enters the standpipe, flows through the 90° elbow (7) and out the fluid drainage pipe, which is connected via a slip union (12) to a pipe that directs fluid from the fish tank to one or more hydroponics tanks, used for growing plants. We observed, that due to the size and activity of the fish, the majority (e.g., at least about 75%) of the fecal material settles at the bottom of the fish tank, allowing the fecal material to move down to the second valve (10) for collection. Generally, the cross-sectional diameter of the inner pipe is governed by the desired flow rate. If the diameter is too large, then the rate for the system and pump will be too fast. If the diameter is too small, then the rate might be too slow and back-up water in the fish tank to the other parts of the system. In various embodiments, a target drainage or fluid flow rate is from about 2 L/min to about 10 L/min, e.g., about 2, 3, 4, 5, 6, 7, 8, 9 or 10 L/min. In industrial scale systems, the flow rate may be faster, e.g., at least about 20 L/min, up to 30, 40, 50, 60, 70, 80, 90 or 100 L/min, depending on the size of the tanks, the size and type of fish, and the size and type of plants cultivated in the system. In some embodiments, the entire. In various embodiments, the inner diameter of the inner pipe is in the range of about 0.5 inches to about 2.0 inches, e.g., at least about 0.5 inch and up to about 1.0 in, 1.5 in or 2.0 in. In some embodiments, the inner pipe has a diameter of 1 in.

The standpipe (2) stands in the fish tank at roughly the same height as the water in the fish tank, low enough to drain to run water from the fish tank to the plant tank. The standpipe (2) is of a sufficient length to span the height of a desired water level in the tank and extend through the drain orifice in the tank into the outer pipe into an interior of the 3-way T connector (6), however. In some embodiments, the length of the standpipe (2) is in the range of about 20 inches to about 50 inches, e.g., at least about 20 inches and up to about 25, 30, 35, 40, 45, 50 inches. In some embodiments, the top of the stand pipe has a slip cap with one or more drilled holes, e.g., that provides a safety mechanism to prevent the system from over flowing, e.g., in case there is a clog or a pump fails. Generally, the slip cap has 2, 3, 4, 5 or 6 holes of an average diameter of about 0.2 in. to about 0.5 in, e.g., about 0.25 in. In some embodiments, the standpipe has one or more slits on the side, e.g., that facilitates regulation of the water level. In various embodiments, the slits are cut into the standpipe to be below the surface of the water, e.g., about 4-10 inches below the surface of the water or below the top of the standpipe, e.g., about 4, 5, 6, 7, 8, 9 or 10 inches below the surface of the water or below the top of the standpipe. The slits are wide enough so that water can flow down the standpipe, but narrow enough that the fish cannot enter the standpipe. In some embodiments, the slits have a width in the range of about 2-10 mm, e.g., about 2, 3, 4, 5, 6, 7, 8, 9, 10 mm. In come embodiments, the slits have an arc length of about 90° to about 120° of the circumference of the standpipe, e.g., about 90°, 100°, 110° or 120° of the standpipe. In some embodiments, two slits at the same level are cut into the standpipe. The standpipe (2) is connected to a 90° elbow (7). The ends of the standpipe (2) can be male, female, threaded or unthreaded, as appropriate to form a sealed connection with the 90° elbow (7). In some embodiments, one or both ends of the standpipe (2) are male.

The 90° elbow connector (7) is positioned within a 3-way T connector (6) in the outer pipe. The 90° elbow (7) generally will have the same cross-sectional diameter as the standpipe (2) to which it is connected. The 90° elbow is selected to fit within a 3-way T connector and to not have sharp angles, e.g., is curved or sweeping, e.g., short sweep elbow, such that solids do collect in the elbow, which can lead to bacterial growth. The ratio of the diameter of an orifice of the 3-way T connector (6) to the cross-sectional diameter of the 90° elbow connector (7) is generally at least about 2:1, and can be as much as 2.5:1, 3:1, 3.5:1, 4:1, or more. The 90° elbow connector (7) is connected to a fluid drainage pipe (8). The ends of the 90° elbow connector (7) can be male, female, threaded or unthreaded, as appropriate to form sealed connections with the standpipe (2) and the fluid drainage pipe (8). In some embodiments, both ends of the 90° elbow connector (7) are female.

The fluid drainage pipe (8) extends from the interior of the 3-way T connector (6) at about 90° from the standpipe (2) and horizontally or substantially horizontally in relation to the surface of the water. The fluid drainage pipe (8) generally will have the same cross-sectional diameter as the 90° elbow connector (7) and the standpipe (2) to which it is connected. A slip reducer (11) connected to the 3-way T connector (6) seals around the fluid drainage pipe (8). In various embodiments, the fluid drainage pipe has a length in the range of from about 5 inches to about 6, 7, 8, 9 or 10 inches. The ends of the fluid drainage pipe (8) can be male, female, threaded or unthreaded, as appropriate to form sealed connections with the 90° elbow and a slip union (12). In some embodiments, both ends of the fluid drainage pipe (8) are male.

The fluid drainage pipe (8) is connected to a slip union. The "slip union" is a re-usable connection point in the inner pipe line. It allows for the ready installation and detachment of the effluent sampling system from the rest of the recirculating system, as well as allowing for easier replacement and cleaning of plumbing elements throughout the system. In some embodiments, the slip union is female.

b. Outer Pipe

The outer pipe comprises (i) a bulkhead (3) capable of forming a drain orifice in the fish tank connected to (ii) a connector pipe (5) that connects the bulkhead to a (iii) 3-way T connector (6); (iv) a slip reducer (11) connected to the 3-way T connector, wherein the slip reducer seals around the fluid drainage pipe (8) of the inner pipe; (v) a first valve (9) connected to the 3-way T connector (6); and (vi) a second valve (10) connected to the first valve. The elements of the outer pipe have a wider cross-sectional diameter than the elements of the inner pipe. Further, elements of the outer pipe can have the same or different diameters. For example, in some embodiments, the 3-way T connector (6) can have a wider diameter than the first valve (9) and/or second valve (10), e.g., to accommodate the 90° elbow (7). In embodiments where elements of the outer pipe are of different diameters, additional "slip reducer" or "reducer coupling" connecting pipes having a narrow end and a wide end can be used to connect elements having different diameters. The outer pipe can further include connecting pipes between the 3-way T connector (6) and the first valve (9) and/or between the first valve (9) and the second valve (10).

In some embodiments, the outer pipe has an inner diameter in the range of about 1.0 inches to about 4.0 inches, e.g., at least about 1.0 inch and up to about 1.5 in, 2.0 in, 2.5 in, 3.0 in, 3.5 in or 4.0 in. In some embodiments, the length of the outer pipe from the top of the bulkhead to the bottom of the second valve is in the range of about 10 inches to about 50 inches, e.g., at least about 10 inches and up to about 12, 14, 16, 18, 20, 22, 24, 26, 28, 30, 32, 34, 36, 38, 40, 42, 44, 46, 48 or 50 inches. In some embodiments, the length of the outer pipe from the top of the bulkhead to the center of the 3-way tee is in the range of about 5 inches to about 20 inches, e.g., at least about 5 inches and up to about 6, 7, 8, 9, 10, 11, 12, 13, 14, 15, 16, 17, 18, 19, 20 inches.

The bulkhead (3) can form a drain in the fish tank and the standpipe is inserted through the orifice of the bulkhead. The top of the bulkhead, or the bulkhead surface in the inside of the fish tank can further have a screen insert in the orifice of the bulkhead (3) and sealing around the standpipe (2), wherein the screen insert comprises openings sufficiently large to allow fish feces to flow into the outer pipe and sufficiently small to prevent fish from entering the outer pipe. In some embodiments, the outer pipe further comprises a terminal adaptor (4) connecting the bulkhead (3) to a connector pipe (5). Either or both of the terminal adaptor (4) and the connector pipe (5) can be "slip reducer" or "reducer coupling" connecting pipes. The bulkhead (3) is connected to the 3-way T connector (6), e.g., via a terminal adaptor and/or a connecting pipe. In some embodiments, the terminal adaptor and/or the connecting pipe have a diameter in the range of 2 inches to 2.5 inches. The ends of the bulkhead (3), the terminal adaptor (4) and the connector pipe (5) can be male, female, threaded or unthreaded, as appropriate to form sealed connections with the 90° elbow and the slip union (12). In some embodiments, the bulkhead (3) has internal and external threads, where the external threads are left handed and used solely for the purpose of using the jam nut to secure the seal against the tank. In some embodiments, the terminal adaptor (4) is inserted or screwed into the female threads of the bulkhead. In some embodiments, a connector pipe (5) is slipped or screwed into the terminal adaptor (4). In such an embodiment, the connector pipe (5) is male and this portion of the terminal adaptor (4) is female. In some embodiments, the connector pipe (5) has a length of about 3 inches to about 4, 5, 6, 7, 8, 9, 10 inches, and the ends of the connector pipe (5) can be male, female, threaded or unthreaded, as appropriate.

The 3-way T connector (6) has orifices of a diameter sufficiently wide to accommodate the 90° elbow and such that effluent solids do not collect (e.g., sufficient to clog) in the interior space of the 3-way T connector. The orifices of the 3-way T connector (6) are arranged orthogonally in x-y-z planes so that two orifices are 180° from each another and a third orifice is 90° from the first two. The third orifice, extending 90° from the first two, is connected to a slip reducer (11) that seals around the fluid drainage pipe (8) of the inner pipe. The orifices of the 3-way T connector (6) can have diameters that are the same or different. In some embodiments, the orifices of the 3-way T connector (6) are 2.5 inches in diameter. The 3-way T connector (6) is connected to the first valve (9), optionally, via a connecting pipe (5) which can be a reducer coupling. The orifices of the 3-way T connector (6) can be male, female, threaded or unthreaded, as appropriate to form sealed connections with connecting pipes (5), the first valve (9) and the reducing slip (11) that seals around the fluid drainage pipe (8). In some embodiments, the three orifices of the 3-way T (6) are all female. As needed, connecting pipes (5) and reducing couplings in the outer pipe can be female on both ends, male on both ends, or female on one end and male on one end. In some embodiments, the connector pipe (5) has a length of about 3 inches to about 4, 5, 6, 7, 8, 9, 10 inches, and the ends of the connector pipe (5) can be male, female, threaded or unthreaded, as appropriate.

The first valve (9) can be a ball valve, a butterfly valve, a gate valve, a globe valve, a check valve and a stop valve. In some embodiments, the first valve (9) is a ball valve. When open, the diameter or fluid passageway of the interior of the first valve (9) should freely allow passage of effluent through the first valve into the second valve. The diameter of the first valve (9) can be the same or different from the 3-way T connector (6) or the second valve (10). In some embodiments, the first valve (9) has a diameter in the range of 2 inches to 2.5 inches. The first valve (9) is connected to the 3-way T connector (6) and the second valve (10), optionally, via connecting pipes (5), which can be reducer couplings. The ends of the first valve (9) can be male, female, threaded or unthreaded, as appropriate to form sealed connections with connecting pipes (5), the second valve (10) and/or the 3-way T connector (6). In some embodiments, the connecting ends of the first valve (9) are both female. In some embodiments, the connector pipe (5) has a length of about 3 inches to about 4, 5, 6, 7, 8, 9, 10 inches, and the ends of the connector pipe (5) can be male, female, threaded or unthreaded, as appropriate.

The second valve (10) can be a ball valve, a butterfly valve, a gate valve, a globe valve, a check valve and a stop valve. In some embodiments, the second valve (10) is a ball valve. The second valve (10) can be the same or different from the first valve (9). When open, the diameter or fluid passageway of the interior of the first valve (10) should freely allow passage of effluent from the outside pipe for collection. The diameter of the first valve (10) can be the same or different from the 3-way T connector (6) or the first valve (9). In some embodiments, the first valve (9) has a diameter in the range of 2 inches to 2.5 inches. The first valve (9) is connected to the 3-way T connector (6) and the second valve (10), optionally, via connecting pipes (5), which can be reducer couplings. The ends of the first valve (9) can be male, female, threaded or unthreaded, as appropriate to form sealed connections with connecting pipes (5), the second valve (10) and/or the 3-way T connector (6). In some embodiments, the connecting ends of the second valve (10) are both female.

c. Fish Tank

In some embodiments, the sampling system further comprises a fish tank. In some embodiments, the fish tank is made of fiber glass. In some embodiments, the fish tank has a volume in the range of about 5 L to about 500 L, e.g., at least about 5 L and up to about 10 L, 20 L, SOL, 75 L, 100 L, 110 L, 120 L, 130 L, 140 L, 150 L, 200 L, 250 L, 300 L, 350 L, 400 L, 450 L or 500 L. In some embodiments, the drain orifice of the fish tank is in a bottom surface of the tank. In some embodiments, the drain orifice of the fish tank is in a side surface of the tank. In some embodiments, the fish tank comprises one or more hydroponics rafts. In some embodiments, the sampling system further comprises a hydroponics tank, the hydroponics tank comprising one or more hydroponics rafts.

In some embodiments, the hydroponics tank is in fluid communication with the fish tank. In a recirculating aquaponics system (RAS), the fish tank, the hydroponics tank, and the sump tank, are in fluid communication due to the closed system (e.g., there is no fresh water entering the system unless it is manually entered to replace water that had been removed). In some embodiments, the bottom surface of the fish tank is elevated sufficiently higher than the water surface level of the hydroponics tank to allow for water to flow from the fish tank to the hydroponics tank via gravity. In some embodiments, the bottom surface of the fish tank is elevated at least 12 inches higher, e.g., from about 12 inches to 13, 14, 15, 16, 17, 18, 19, 20, 21, 22, 24, or more, inches higher than the bottom or top surface of the hydroponics tank to allow for water to flow from the fish tank to the hydroponics tank via gravity.

In some embodiments, the sampling system is in fluid communication with a recirculating aquaponics system (RAS), and effluent can be removed from the second valve while water continuously circulates from the fish tank to the hydroponics tank. In some embodiments, the water recirculates at a rate in the range of about 2 L/min to about 10 L/min, e.g., about 2, 3, 4, 5, 6, 7, 8, 9 or 10 L/min. In some embodiments, the water volume in the RAS recirculates or turns over every 1 to 4 hours, e.g., every 1, 1.5, 2, 2.5, 3, 3.5 or 4 hours. In some embodiments, the fish tank and the hydroponics tank are in fluid communication with a sump tank. Generally, in-flow of water from the sump tank is the same rate as the water draining down the standpipe. Physical contamination, e.g., due to splashing, can be reduced or eliminated by separating the tanks and also making a fish tank lid, as well as by decreasing the flow rate to the air lines for the air stones in the plant tank (e.g., prevent bubbles and water splashing).

3. Methods of Containment and Sampling

The effluent sampling system finds use for containment and sampling of fish tank effluent, particularly solid effluent.

With respect to containment, provided are methods of are methods of containing solid effluent from fish in a fish tank. In some embodiments, the methods comprise:

(a) providing an effluent sampling system of claim 20, wherein the fish tank comprises one or more live fish; and (b) allowing effluent, e.g., including solids from the fish which have settled to the bottom of the fish tank, to pass through the first valve (9) in the outer pipe and collect in the second valve (10); whereby the solid effluent from the fish in the fish tank is contained in the second valve (10). In some embodiments, surface water in the fish tank flows through the standpipe, e.g., and further to a hydroponics tank.

With respect to sampling, provided are methods of sampling effluent from a fish tank. In some embodiments, the methods comprise:

(a) providing an effluent sampling system comprising a fish tank, as described above and herein, wherein the fish tank comprises one or more live fish;

(b) allowing effluent, e.g., including solids from the fish which have settled to the bottom of the fish tank, to pass through the first valve (9) in the outer pipe and collect in the second valve (10);

(c) blocking fluid flow through the first valve (9) and opening the second valve (10) to release the collected effluent; and (d) sampling the contents of the collected effluent. In some embodiments, the effluent comprises fish feces. In some embodiments, the fish feces are evaluated for the presence of a foodborne pathogen. In some embodiments, the foodborne pathogen is bacterial, viral and/or parasitic. In some embodiments, the foodborne pathogen is a bacterial pathogen from a bacteria genus selected from the group consisting of *Salmonella*, *Vibrio*, *Campylobacter*, *Escherichia coli* (e.g., *E. coli* O157:H7), *Listeria* (e.g., *Listeria monocytogene*), and *Yersinia*. In some embodiments, the collected effluent is evaluated for the quantities and/or ratios of one or more of carbon, oxygen, nitrogen, phosphorus, ammonia, nitrite, nitrates, pH, temperature, conductivity, dissolved oxygen, % oxygen, C:N ratio, nutrients, contaminants, toxins, heavy metals, pesticides and antibiotics.

In some embodiments of the containment and sampling methods, the fish tank comprises one or more hydroponics rafts. In some embodiments of the containment and sampling methods, the fish tank is in fluid communication with a hydroponics tank. In some embodiments of the containment and sampling methods, the sampling system is in fluid communication with a recirculating aquaponics system (RAS), and effluent can be removed from the second valve while water continuously circulates from the fish tank to the hydroponics tank.

4. Kits

Further provided are kits comprising the elements for assembling the inner pipe and the outer pipe of the effluent sampling system, as described above and herein. In some embodiments, the kit further comprises instructions for assembling the fish tank effluent sampling system. In some embodiments of the kit, the 90° elbow connector (7) is provided fitted inside of the 3-way T connector (6).

In some embodiments, the kit further comprises a cylindrical guide tool for fitting the 90° elbow connector (7) inside of the 3-way T connector (6). The cylindrical guide tool can be provided as a separate element in the kit, or already fitted into the inside of the 3-way T connector (6).

Figure 9:
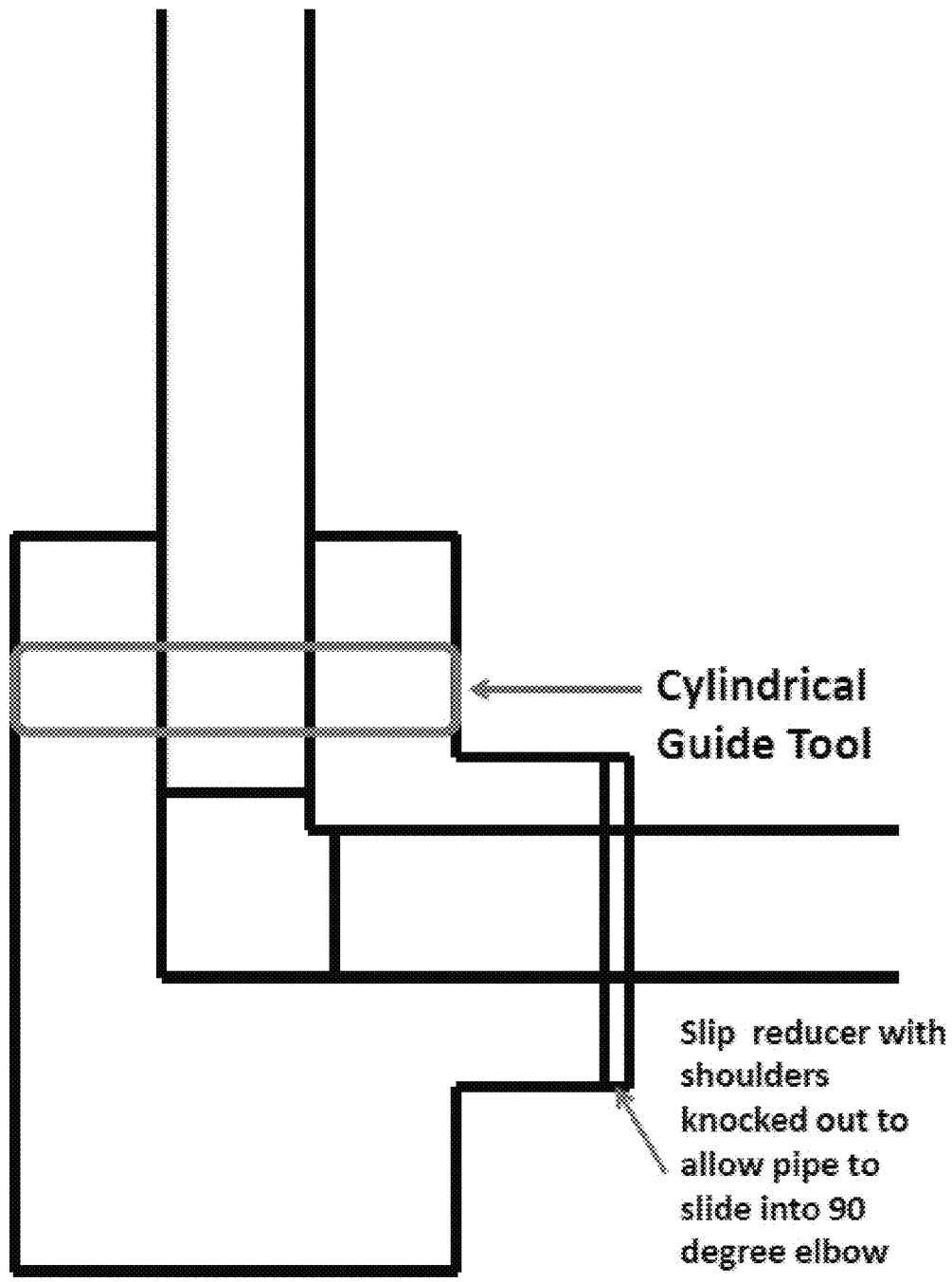
FIG. 9 provides a schematic of the of the cylindrical guide or insertion tool fitted in the 3-way T connector. The standpipe (2) and 90 degree elbow (7) is inserted into the 3-way T (6). The cylindrical guide or insertion tool is then placed onto the standpipe (2) to slide down to inside the 3-way T (6), just above the 90 degree elbow (7). Prior to placing the slip reducer onto the 3-way T (6), the inside slip shoulders (to prevent the pipe from sliding) are knocked out. Large amounts of glue are then placed on the fluid drainage pipe (8), coming through the slip reducer to the elbow. This allows for a tight seal from the fluid drainage pipe (8) to the 90 degree elbow (7) and slip reducer. As the fluid drainage pipe (8) is slid into the slip reducer to the 90 degree elbow (7), the cylindrical guide or insertion tool provides a brace and strength for the glue to seal around the pipe and the elbow, since the tool braces against the back side of the 3-way T (6). The cylindrical guide or insertion tool is removed prior to assembly of the outer pipe.

The dimensions of the cylindrical guide tool will be guided by the inner diameter of the 3-way T connector (6) and the outer diameter of the 90° elbow connector (7). The outer diameter of the cylindrical guide tool is such that the tool fits snugly within the 3-way T connector (6). See, FIG. 9. The inner diameter of the guide is sufficiently wide to allow ready passage of the 90° elbow connector (7) through the cylindrical guide tool, e.g., is at least about 0.5, 0.6, 0.7, 0.8, 0.9 or 1.0 inches wider that the outer diameter of the 90° elbow connector (7). In embodiments where the 3-way T connector (6) has 2.5 in. orifices and the 90° elbow connector (7) has a diameter of about 1 in., the outer diameter of the guide is about 2.5 in., the inner diameter is about 1.4 in., the height is about 1.5 in, and the thickness of the cylinder is about 0.55 in. The cylindrical guide tool is made of a solid material, e.g., wood, metal or plastic, of sufficient hardness to withstand (e.g., not flex against) the pressure of pushing 90° elbow connector (7) into the 3-way T connector (6) such that the elbow connector can be positioned into the 3-way T connector (6). In order to achieve a sealed connection between the fluid drainage pipe (8) and the 90 degree elbow (7) inside the 3-way T (6), the cylindrical guide tool serves as a brace against the inside of the 3-way T (6) wall. Also, the cylindrical guide tool is constructed to be readily inserted into and removed from the 3-way T connector (6) once the 90° elbow connector (7) has been positioned, and before the 3-way T connector (6) is connected to assemble the outer pipe. In some embodiments, the cylindrical guide tool is made of wood, e.g., of pine or a wood of similar density, e.g., having a density in the range of about 350-700 $kg/m^3$ or about 20-55 $lb/ft^3$.

EXAMPLES

The following examples are offered to illustrate, but not to limit the claimed invention.

Example 1

Assessment of Zoonotic Risks in Aquaponic Lettuce Production: A Prototype for Experimental Greenhouse Trials Background Aquaponics is the integration of aquaculture and hydroponics that is now being used as a model for sustainable food production. Because fresh vegetables are usually consumed raw, there are concerns about food safety and zoonotic risks from fish waste in aquaponic production. The purpose of this study was to determine the survival, persistence, and transfer via root uptake of an attenuated *Salmonella* strain in a recirculating aquaponic system (RAS) used for leafy green production in order to gain the knowledge of good agricultural practices specific for aquaponic practitioners to reduce the potential for foodborne illnesses due to product contamination. A prototype RAS for experimental trials was designed and built at the Center for Aquatic Biology and Aquaculture (CABA) facility at UC Davis. In order to conduct the experiments, we needed to prevent physical contamination, due to splashing, by separating the tanks and also making a fish tank lid, as well as decreasing the flow rate to the air lines for the air stones in the plant tank (e.g., prevent bubbles and water splashing).

Methods

The tilapia, Oreochromis niloticus, purchased from an approved commercial vendor were fingerlings (30-60 g) and were exposed to a Salmonella bacterium, via intra-gastric inoculation. The inoculum was an avirulent Salmonella enterica Typhimurium (aPTVS177), which had a double mutation and was rifampicin tolerant. Previously, it had only been used in mice and chickens for vaccine development and produce safety field trials (Lopez-Velasco, 2013). One hundred and fifty fingerlings were first placed in a holding tank for two weeks before the RAS inoculation challenge as an acclimation period. A subsample of the population was confirmed negative for Francisella spp., Streptococcus spp., and Salmonella spp. bacteria by culture on modified agar media and real time PCR prior to the start of the study. Fish were fed daily (3.5% body weight) commercially available tilapia feed and water quality parameters were monitored daily (temperature) or weekly (dissolved oxygen). After the two weeks, 25 fish were placed into 6 thirty-gallon tanks in the Aquaculture Facility shelter #2, University of California, Davis and assigned to certain inoculum groups or negative controls. Initially, the lethal and infective dose of Salmonella enterica serovar Typhimurium (aPTVS177) strain to naïve tilapia (Oreochromis spp.) fingerlings was determined by intra-gastric challenge. Using two (high and low) non-lethal doses, a second group of fish was challenged and used in a laboratory controlled RAS growing hydroponic lettuce. The groups were;

Group 1: 1 tank with 25 fish inoculated with $10^9$ CFU/100 µl of Salmonella,

Group 2: 1 tank with 25 fish inoculated with $10^9$ CFU/100 µl of Salmonella,

Group 3: 1 tank with 25 fish inoculated with $10^5$ CFU/100 µl of Salmonella,

Group 4: 1 tank with 25 fish inoculated with $10^5$ CFU/100 µl of Salmonella,

Group 5: 1 tank with 25 fish inoculated with 100 µl of phosphate buffered saline (PBS) (BD, Sparks, Md.) for a negative control, and Group 6: 1 tanks with 25 fish inoculated with 100 µl of PBS for a negative control.

Each thirty-gallon fish tanks were connected to another thirty-gallon tank growing 9 butter head lettuce plants (Lactuca sativa var. capitate), two weeks old (Greenhouse, University of California, Davis) with polyvinyl chloride (PVC) (Ace Hardware, Davis, Calif.; Irrigation Supply, Woodland, Calif.; Home Depot, Woodland, Calif.) pipe and a 1000 GPH submergible mechanical pump (Little Shop of Growers, Woodland, Calif.), where the maximum pressure was estimated to be 3-5 psi, to recirculate the water in the closed system. Before intra-gastric administration of the bacteria, fish were anesthetized with buffered MS222 at a dose of 100 mg/L. Protocols by Iwama et al. (1989), Ross and Ross (2008), and Ross (2002) were followed (Iwama, et al., (1989) Can J Zool 67:2065-2073; Ross, et al., (2008) "Anaesthetic and sedative techniques for aquatic animals," Blackwell Science, Oxford, United Kingdom; and Rose (2002) Rev Fisher Sci 10:1-38). Briefly, groups of 25 fish were anesthetized and the bacterium dose (0.1 mL) was administered through an intubated animal feeding disposable needle (Fisherbrand, Hampton, N.H.), attached to a 1 mL syringe (BD, Sparks, Md.) and pushed 3-5 cm into the esophagus so that the end of the tube was positioned in the stomach. After inoculation, the fish were returned to their respective tanks and monitored continuously during recovery until the animal had regained equilibrium and was no longer ataxic. The entire system, animals and plants, were then followed for 6 weeks (42 days) by monitoring daily fish activity and water quality parameters, such as temperature, ammonia, nitrites, nitrates, pH, conductivity, and dissolved oxygen (YSI Pro Plus Meter, YSI, Yellow Springs, Ohio; API Freshwater Master Test Kit, Amazon). All measurements were recorded twice a day, morning and night. On days 01, 07, 14, 21, 28, 35, and 42 post-inoculation (PI), one liter of water from both the fish and plant tanks were collected with a assigned aquatic gravel vacuum (Imagitarium, Amazon), as well as fish waste collected from the fecal release valve into a whirlpak bag (Nasco, Modesto, Calif.) and a composite of five 1M. sump tank bioballs (Pentair, Minneapolis, Minn.) for the presence/enumeration of the inoculated Salmonella with microbiological and molecular analysis. On day 42 PI, in addition to the normal samples, plants were also collected, separated into leaves, roots, starter pots, swabs from each row (3) of the floating Styrofoam plant rafts, filter components from the fish (clay beads) and plant (filter sponge) tanks, and the plant tank biolayer. All fish were euthanized with buffered MS222 (500 mg/L) where the mucus and gastrointestinal tissues were collected for presence/enumeration of the inoculum. Three fish from each system was preserved in 10% neutral buffered formalin for further histopathological examination. Using R statistical software (University of Auckland, New Zealand), a general linear model was preformed to determine significant factors associated with the presence/concentration of the inoculated Salmonella.

RESULTS AND DISCUSSION

We determined that the three highest inoculum doses ($10^8$-$10^{10}$ CFU) resulted in fish with Salmonella positive gastrointestinal tracts and associated tissues. Salmonella recovery during phase 2 is shown in Table 1. On day 42 (harvest), lettuce leaves, roots, pots, and rafts were negative; two fish had positive stomach and intestinal tissues. Dissolved oxygen (mg/L) was the only significant daily water quality parameter associated with Salmonella. Data from this study will fill knowledge gaps regarding how foodborne pathogens may persist and move through an aquaponic system.

TABLE 1

*Salmonella* concentration (Most Probable Number, MPN/g) in RAS components

|  | Samples collected | Day 1 | Day 7 | Day 14 | Day 28* |
|---|---|---|---|---|---|
| System 1 (high inoculum) | Plant water (MPN/mL) | 240 | 0.0061 | <LOD | <LOD |
|  | Fish water (MPN/mL) | 700 | <LOD | <LOD | <LOD |
|  | Feces (MPN/mL) | >700 | 0.45 | 0.23 | >70 |
|  | Bioballs (MPN/g) | 58 | 0.047 | <LOD | <LOD |
| System 2 (high inoculum) | Plant water (MPN/mL) | 240 | <LOD | <LOD | <LOD |
|  | Fish water (MPN/mL) | 700 | <LOD | <LOD | <LOD |
|  | Feces (MPN/mL) | 700 | <LOD | 0.31 | 0.071 |
|  | Bioballs (MPN/g) | 58 | <LOD | <LOD | <LOD |
| System 3 (low inoculum) | Plant water (MPN/mL) | 0.0017 | <LOD | <LOD | <LOD |
|  | Fish water (MPN/mL) | 0.0017 | <LOD | <LOD | <LOD |
|  | Feces (MPN/mL) | <LOD | <LOD | 24 | 0.02 |
|  | Bioballs (MPN/g) | 0.052 | <LOD | <LOD | <LOD |
| System 4 (low inoculum) | Plant water (MPN/mL) | 0.0061 | <LOD | <LOD | <LOD |
|  | Fish water (MPN/mL) | 0.0240 | <LOD | <LOD | <LOD |
|  | Feces (MPN/mL) | 0.046 | <LOD | >70 | 0.086 |
|  | Bioballs (MPN/g) | <LOD | <LOD | <LOD | <LOD |

LOD = limit of detection, 0.00082 MPN/g
*Treatment samples days 35, 42 and controls <LOD It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A fish tank effluent sampling system, comprising:
   (a) an outer pipe for effluent capture, and
   (b) an inner pipe for fluid drainage;
   wherein the outer pipe comprises:
      (i) a bulkhead (3) capable of forming a drain orifice in the fish tank;
      (ii) a connector pipe (5) that connects the bulkhead (3) to a 3-way T connector (6);
      (iii) a 3-way T connector (6);
      (iv) a slip reducer (11) attached to the 3-way T connector (6), wherein the slip reducer (11) seals around the inner pipe;
      (v) a first valve (9) that connects to the 3-way T connector (6); and
      (vi) a second valve (10) that connects to the first valve (9);
   wherein the inner pipe comprises:
      (i) a standpipe (2), wherein the standpipe (2) is of a sufficient length to span the height of a desired water level in the tank and extend through the drain orifice in the tank into the outer pipe into an interior of the 3-way T connector (6), the standpipe (2) connecting to
      (ii) a 90° elbow connector (7) positioned within the 3-way T connector (6) in the outer pipe; and
      (iii) a fluid drainage pipe (8) that connects to the 90° elbow connector (7), the fluid drainage pipe (8) extending from the interior of the 3-way T connector (6) at about 90° from the standpipe (2);
   wherein the inner pipe and the outer pipe are sealed against fluid leakage.

2. The sampling system of claim 1, wherein fluid in the inner pipe is not in fluid communication with effluent in the outer pipe.

3. The sampling system of claim 1, wherein fluid in the inner pipe is sealed against effluent in the outer pipe.

4. The sampling system of claim 1, wherein the outer pipe further comprises a reducing fitting connecting the bulkhead (3) to the connector pipe (5).

5. The sampling system of claim 1, wherein the outer pipe further comprises a terminal adaptor (4) connecting the bulkhead (3) to the connector pipe (5).

6. The sampling system of claim 1, wherein the outer pipe further comprises a connector pipe (5) connecting the 3-way T connector (6) to the first valve (9).

7. The sampling system of claim 1, wherein the outer pipe further comprises a connector pipe (5) connecting the first valve (9) to the second valve (10).

8. The sampling system of claim 1, further comprising a fish tank.

9. The sampling system of claim 8, wherein the fish tank has a volume in the range of about 5 L to about 500 L.

10. The sampling system of claim 8, wherein the fish tank comprises one or more hydroponics rafts.

11. The sampling system of claim 8, further comprising a hydroponics tank, the hydroponics tank comprising one or more hydroponics rafts.

12. The sampling system of claim 11, wherein the fish tank is in fluid communication with the hydroponics tank.

13. The sampling system of claim 12, wherein the sampling system is in fluid communication with a recirculating aquaponics system (RAS), and effluent can be removed from the second valve while water continuously circulates from the fish tank to the hydroponics tank.

14. A method of containing solid effluent from fish in a fish tank, the method comprising:
   (a) providing an effluent sampling system of claim 8, wherein the fish tank comprises one or more live fish; and
   (b) allowing effluent including solids from the fish which have settled to the bottom of the fish tank to pass through the first valve (9) in the outer pipe and collect in the second valve (10); whereby the solid effluent from the fish in the fish tank is contained in the second valve (10).

15. The method of claim 14, wherein the fish tank comprises one or more hydroponics rafts.

16. The method of claim 14, wherein the sampling system is in fluid communication with a recirculating aquaponics system (RAS), and effluent can be removed from the second valve while water continuously circulates from the fish tank to the hydroponics tank.

17. A method of sampling effluent from a fish tank, the method comprising:
(a) providing an effluent sampling system of claim 8, wherein the fish tank comprises one or more live fish;
(b) allowing effluent including solids from the fish in the fish tank to pass through the first valve (9) in the outer pipe and collect in the second valve (10);
(c) blocking fluid flow through the first valve (9) and opening the second valve (10) to release the collected effluent; and
(d) sampling the contents of the collected effluent.

18. The method of claim 17, wherein the effluent comprises fish feces.

19. The method of claim 18, wherein the feces is evaluated for the presence of a foodborne pathogen.

20. A kit comprising:
(a) components (e.g., pipe fittings) for constructing an outer pipe, the outer pipe comprising:
(i) a bulkhead (3) capable of forming a drain orifice in a fish tank;
(ii) a connector pipe (5) that connects the bulkhead (3) to a 3-way T connector (6);
(iii) a 3-way T connector (6);
(iv) a slip reducer (11) that is capable of sealing around the inner pipe;
(v) a first valve (9) that connects to the 3-way T connector (6); and
(vi) a second valve (10) that connects to the first valve (9); and
(b) components for constructing an inner pipe, the inner pipe comprising:
(i) a standpipe (2);
(ii) a 90° elbow connector (7) that can be positioned within the 3-way T connector (6) in the outer pipe; and
(iii) a fluid intake pipe (8) that connects to the 90° elbow connector (7).

\* \* \* \* \*

UNITED STATES PATENT AND TRADEMARK OFFICE
CERTIFICATE OF CORRECTION

Page 1 of 1

PATENT NO. : 11,234,681 B2
APPLICATION NO. : 16/276071
DATED : February 1, 2022
INVENTOR(S) : Michele T. Jay-Russell et al.

It is certified that error appears in the above-identified patent and that said Letters Patent is hereby corrected as shown below:

In the Specification

In Column 3, Line 4, please replace "SOL" with --- 50L ---;

In Column 5, Line 36, please replace "SOL" with --- 50L ---;

In Column 8, Line 41, please replace "SOL" with --- 50L ---;

In Column 12, Line 35, please replace "SOL" with --- 50L ---; and

In the Claims

In Column 19, Claim 20, Line 17, please delete "(e.g., pipe fittings)".

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*